(12) United States Patent
Shippert

(10) Patent No.: US 8,333,740 B2
(45) Date of Patent: Dec. 18, 2012

(54) TISSUE TRANSFER CANNULA

(76) Inventor: Ronald D. Shippert, Littleton, CO (US)

( * ) Notice: Subject to any disclaimer, the term of this patent is extended or adjusted under 35 U.S.C. 154(b) by 583 days.

(21) Appl. No.: 12/434,073

(22) Filed: May 1, 2009

(65) Prior Publication Data

US 2010/0280496 A1  Nov. 4, 2010

(51) Int. Cl.
*A61M 5/31* (2006.01)
(52) U.S. Cl. ........................................ 604/239; 604/535
(58) Field of Classification Search .................. 604/239, 604/96.01, 164.01, 523, 533–284, 128–129
See application file for complete search history.

(56) References Cited

U.S. PATENT DOCUMENTS

| | | | |
|---|---|---|---|
| 1,162,896 A | 12/1915 | Achberger | |
| 1,188,180 A * | 6/1916 | Kells | 604/45 |
| 1,217,287 A | 2/1917 | Dillinger | |
| 1,730,820 A | 10/1929 | Holden | |
| 2,520,355 A | 8/1950 | Bell | |
| D182,827 S | 5/1959 | Latham | |
| D193,496 S | 8/1962 | Jacoff | |
| D221,614 S | 8/1971 | McMahon et al. | |
| D230,468 S | 2/1974 | Fairbairn | |
| D245,062 S | 7/1977 | Grame | |
| 4,106,505 A | 8/1978 | Salter et al. | |
| D252,554 S | 8/1979 | Lancer | |
| D260,869 S | 9/1981 | West et al. | |
| 4,414,438 A | 11/1983 | Maier et al. | |
| 4,445,011 A | 4/1984 | Hansen | |
| 4,885,818 A | 12/1989 | Arterbury | |
| 4,926,521 A | 5/1990 | Gagnepain | |
| 4,950,013 A | 8/1990 | Yonkers | |
| 5,100,395 A * | 3/1992 | Rosenberg | 604/284 |
| 5,299,497 A | 4/1994 | Dias | |
| 5,338,294 A | 8/1994 | Blake, III | |
| D355,831 S | 2/1995 | Hull et al. | |
| D357,947 S | 5/1995 | Richer | |
| 5,440,784 A | 8/1995 | Hull et al. | |
| 5,477,852 A | 12/1995 | Landis et al. | |
| 5,536,259 A | 7/1996 | Utterberg | |
| D373,944 S | 9/1996 | Thompson et al. | |
| D389,720 S | 1/1998 | Warner et al. | |
| D393,791 S | 4/1998 | Halls et al. | |
| 5,737,803 A | 4/1998 | Tisdale | |
| 5,761,767 A | 6/1998 | Barton | |
| 5,762,629 A | 6/1998 | Kambin | |
| 5,802,960 A | 9/1998 | Graj et al. | |
| 5,805,256 A | 9/1998 | Miller | |
| D399,722 S | 10/1998 | Eidsmoe et al. | |
| 5,817,050 A | 10/1998 | Klein | |

(Continued)

FOREIGN PATENT DOCUMENTS

WO   WO 2006/026969   3/2006

*Primary Examiner* — Kevin C Sirmons
*Assistant Examiner* — Phillip Gray
(74) *Attorney, Agent, or Firm* — Sheridan Ross P.C.

(57) ABSTRACT

Cannula and handle systems and cannulas having substantially continuous interior pathways or channels are provided. The interior pathway may extend from the inlet to the cannula to the outlet, such that tissue collected at the inlet is carried to the outlet without contacting other components. Moreover, the substantially continuous nature of the interior pathway, with an absence of drop-offs, blind pockets or other discontinuities, facilitates cleaning. In addition, inlet holes are sized to promote the transfer of tissue through the channel to the outlet, and to the avoidance of damaging collected tissue.

15 Claims, 5 Drawing Sheets

U.S. PATENT DOCUMENTS

| | | |
|---|---|---|
| 5,817,071 A | 10/1998 | Dewindt et al. |
| D403,228 S | 12/1998 | Halls et al. |
| D403,946 S | 1/1999 | Shih |
| D404,280 S | 1/1999 | Wen |
| 5,964,761 A | 10/1999 | Kambin |
| D425,365 S | 5/2000 | Chien |
| 6,065,188 A | 5/2000 | Wold et al. |
| D426,135 S | 6/2000 | Lee |
| D426,136 S | 6/2000 | Yu |
| D427,030 S | 6/2000 | Wen |
| D454,048 S | 3/2002 | Lin |
| 6,530,125 B2 | 3/2003 | Shippert |
| 6,595,215 B2 | 7/2003 | Wood |
| 6,676,677 B2 | 1/2004 | Klein |
| 6,807,967 B2 | 10/2004 | Wood |
| 7,059,328 B2 | 6/2006 | Wood |
| 7,188,642 B2 | 3/2007 | James et al. |
| 7,276,055 B2 | 10/2007 | DeWindt et al. |
| 2003/0161816 A1 | 8/2003 | Fraser et al. |

* cited by examiner

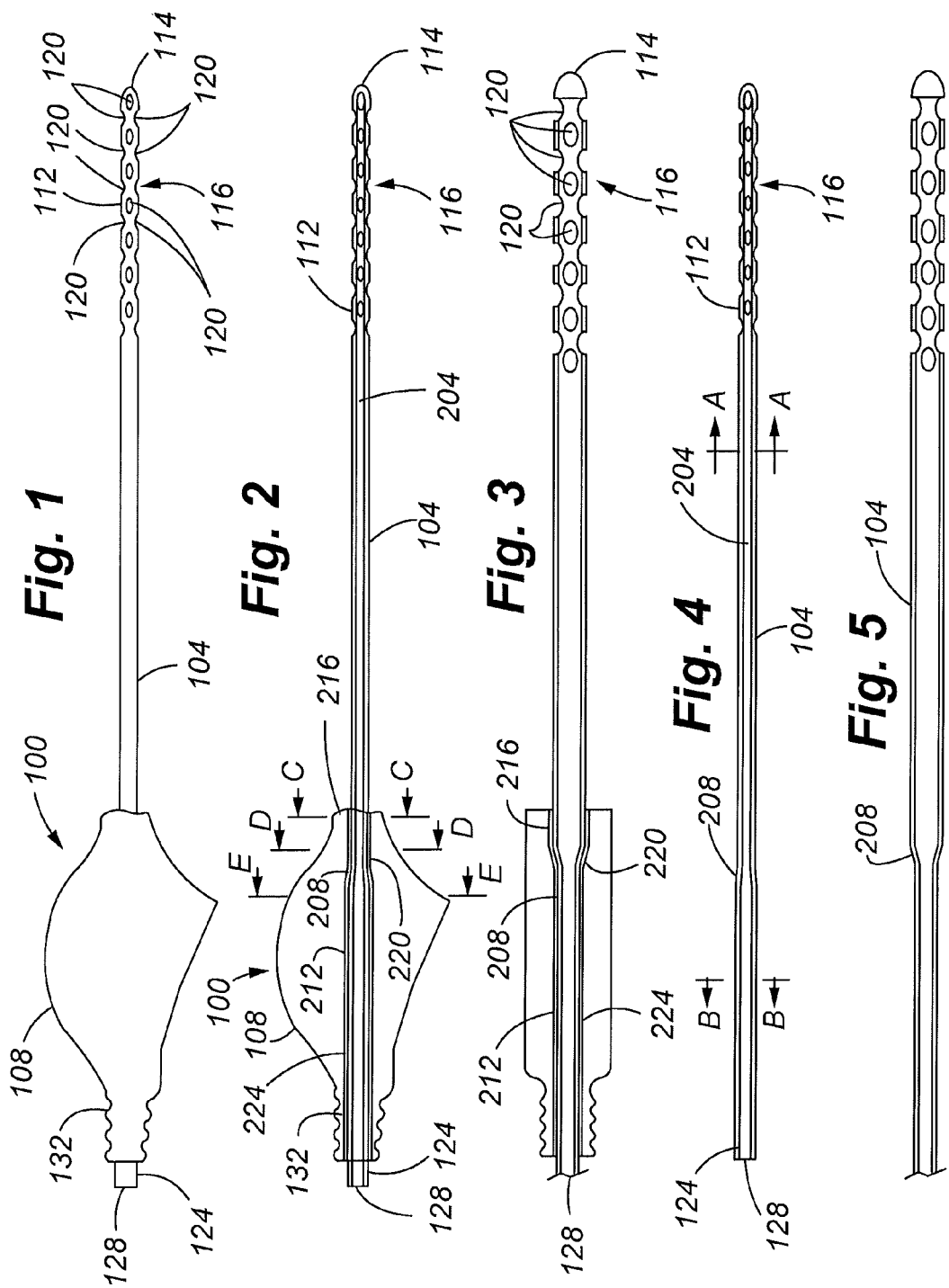

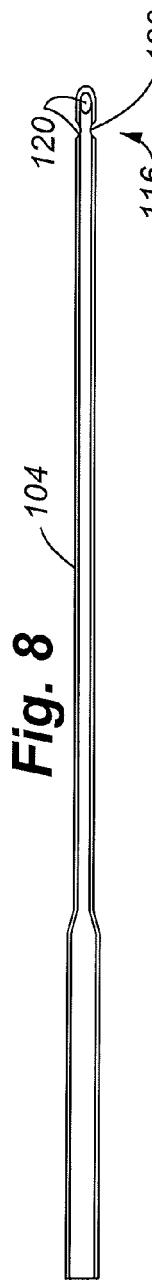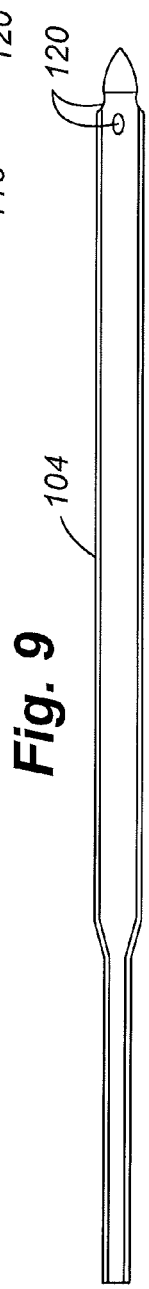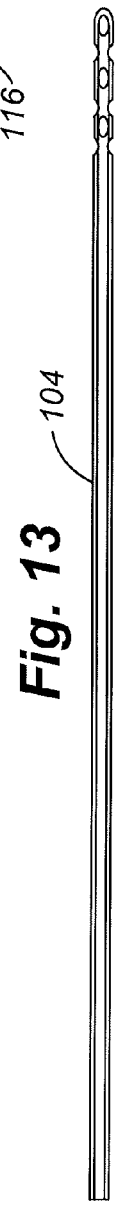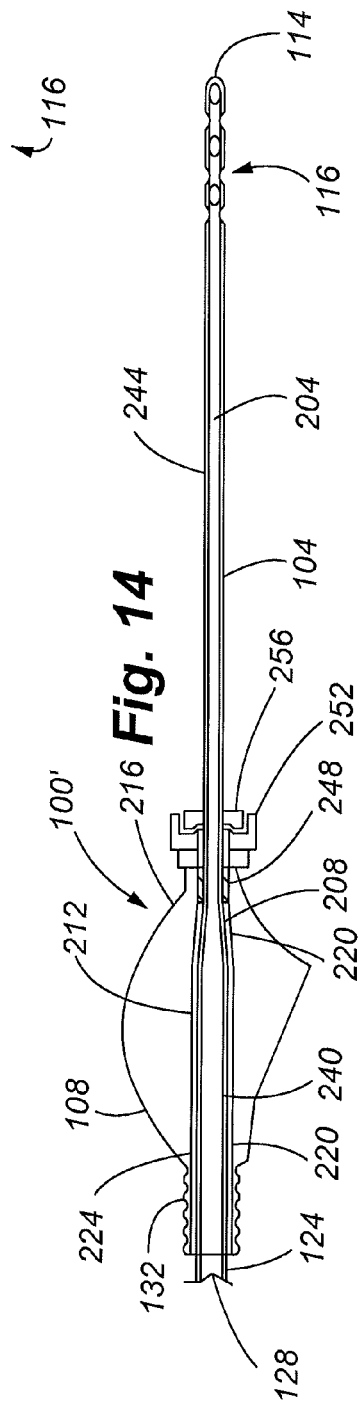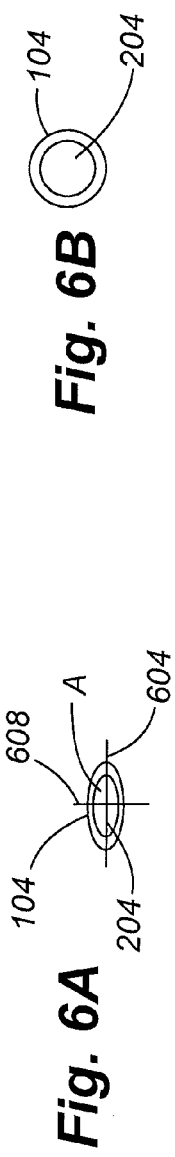

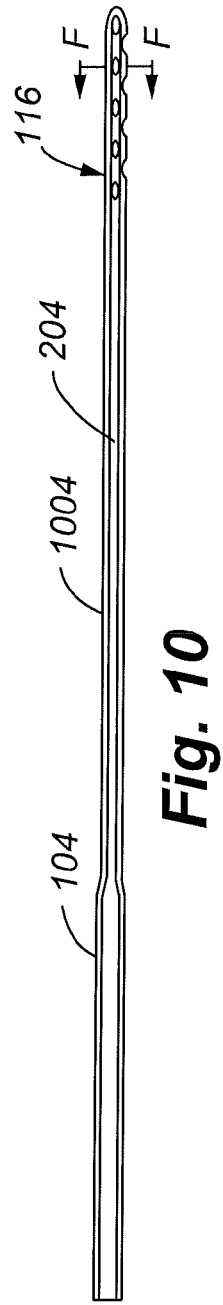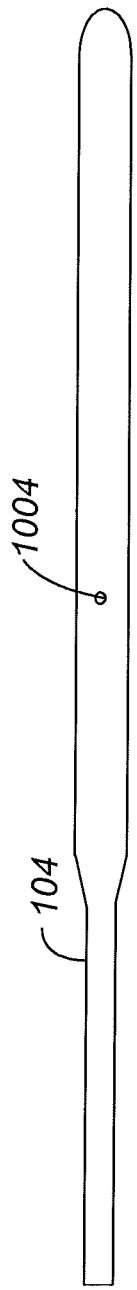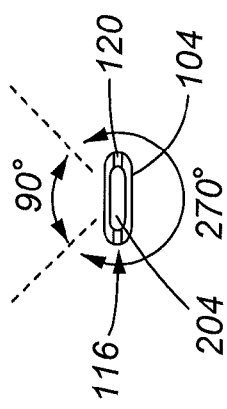

TISSUE TRANSFER CANNULA

FIELD

A tissue transfer cannula and method for producing a tissue transfer cannula are disclosed. More particularly, a tissue transfer cannula with a substantially continuous interior pathway and method for producing such a cannula are disclosed.

BACKGROUND

Microlipoinjection is a process in which fat is taken by a cannula from one spot in the body and reinjected in another place in the body. Microlipoinjection has also been known as liposuction with fat transfer, fat grafting or fat transplantation. In general, microlipoinjection is performed to treat divots and scar indentations from trauma to the face or body, such as may occur as a secondary effect of domestic trauma, surgery or infection. Microlipoinjection can also be used to treat the effects of the loss of the subcutaneous layer of fat due to the normal aging process, either alone or in combination with facelift and fat grafting techniques. Microlipoinjection can also be used for providing filler to reapproximate weakened vocal cords, fill sinuses, or partially close incompetent valves.

In addition, every mass of fat in the human body has with it a varying number of adult stem cells. These stem cells are the precursor to healthy fat cells. In addition to readily developing into normal fatty tissue, they have a limited ability to differentiate into different tissue. When placed in fat they will divide several times into mature fat cells and more adult stem cells. These stem cells are an important part of a tissue harvest.

Up to about 1990, there were few artificial filler substances available to surgeons. Accordingly, surgeons used human bone, collagen and fat as fillers. However, the use of fat was not very successful, because the instruments and techniques were not sufficiently refined. For example, 50% of the fat may not have lived through the transplantation process. As a result, surgeons would need to implant more fat than would be required if all of the fat survived the process, or the transplantation process would have to be repeated multiple times or both.

More recently, a number of filler substances, such as Restylane Hyaluronic Acid, Collagen, Fibril, ePTFE (Teflon®), Hylan B Gel, Artecol, BioBlastique and have been used. These substances have proved effective at filling small areas, but the cost for larger areas has become prohibitive. For this reason, as well as interest in the "natural substance" concept, surgeons and their patients have again looked at using fat as a filler.

With the renewed interest in using fat as a filler, techniques have been refined to provide a better fat graft "take" with revascularization. However, the instruments and devices conventionally available to perform the procedure remain clumsy and ill-suited for the procedure.

Commonly available liposuction handles and cannulas often have severe drop-offs, blind pockets, or other discontinuities in the tissue pathway. These discontinuities result in an instrument that is difficult or impossible to clean. In addition, two piece instruments featuring separable handle and cannulas can make cleaning the instrument even more difficult where at least some portion of the tissue pathway is formed by the handle. In particular, discontinuities in the interior pathway of the cannula and/or handle creates drop-offs or blind pockets that are difficult or impossible to clean. For example, tissue can become impacted in such areas, posing a risk of contamination. Typical systems that feature separable cannulas and handles can also be expensive to manufacture, because of the fittings required to effect a secure connection between the cannula and handle.

In addition to drop-offs, blind pockets and other discontinuities along the length of a tissue transfer channel, typical cannulas often include blind pockets at their tip, which are difficult or impossible to clean. The shape of the outer surface of cannulas also can be such that the practitioner using the instrument must exercise special care to avoid damage to tissue that is not to be removed from the body.

Accordingly, it would be desirable to provide a cannula and/or a cannula and handle system that was easy to clean. In addition, it would be desirable to provide a system in which a cannula could be secured to a handle in a secure fashion, and that was economical to produce. It would also be desirable to provide a cannula that removed tissue to be transferred efficiently, and with reduced damage to that tissue and to neighboring tissue.

SUMMARY

Embodiments of the disclosed invention are directed to solving these and other problems and disadvantages of the prior art. In accordance with embodiments of the disclosed invention, a cannula with an interior pathway or channel that is without discontinuities that can be difficult or impossible to clean is provided. In addition, the inlet to the cannula is formed such that no blind pocket is created at a distal end of the cannula. In accordance with still other embodiments of the disclosed invention, at least a portion of the outer surface of the cannula is non-circular, to facilitate securing the cannula to a cannula handle.

A cannula in accordance with embodiments of the disclosed invention includes an inlet comprising one or more holes. The hole or holes at the most distal end of the interior pathway coincide with and/or define the distal end of the interior pathway. Accordingly, no blind pocket or pockets are formed. In addition, the hole or holes of the inlet can be sized so that they each have an area that is less than the cross-sectional area of the interior pathway of the cannula. Smaller holes produce smaller fat parcels, which pass through the cannula faster secondary to less friction on the walls. In accordance with still other embodiments of the disclosed invention, the inlet includes a plurality of holes that extend along or span no more than two inches of the distal end of the cannula. From the inlet at the distal end of the cannula to the outlet at the proximal end of the cannula, the interior pathway is substantially continuous, without any drop-offs, blind pockets or other discontinuities.

A cannula and handle system in accordance with embodiments of the disclosed invention can include a handle with a receiving channel. When the cannula and handle system is assembled for use, the distal end of the cannula extends from a first or distal end of the handle, while the proximal end of the cannula extends from the second or proximal end of the handle. Moreover, no portion of the handle defines the interior pathway along which tissue is transported. Instead, the interior pathway, from the inlet to the outlet, is defined entirely by the cannula. Accordingly, the cannula includes the only portion of the cannula and handle system through which tissue that is harvested for reinjection is passed.

The distal portion of the cannula can include an outer surface that is non-circular in cross-section. This can provide a secure connection between the cannula and handle of a cannula and handle system. A corresponding portion of a receiving channel of the handle can mate with at least a portion of the non-circular surface of the cannula, preventing rotation of the cannula relative to the housing. In addition, a transition between the non-circular portion and another portion of the cannula can, together with a corresponding portion of the handle receiving channel, form a stop that prevents movement of the cannula relative to the handle in a first direction along a longitudinal axis of the cannula, as well as preventing rotation of the cannula relative to the handle. In accordance with further embodiments of the disclosed invention, the non-circular outer surface of the cannula may extend from the tip of the cannula to a section of the cannula that is received by the handle when the handle and cannula are joined to one another. By providing an oval or flattened distal end, dermal damage resulting in subcutaneous scarring can be reduced as compared to a round cannula. In accordance with still other embodiments, the cannula can be in two pieces, with a first piece that extends through and is integral with the handle, and a second piece that includes the inlet and that is interconnected to the first piece.

A method in accordance with embodiments of the disclosed invention for producing a cannula includes plugging a tubular member at one end, to form the tip of the cannula. An inlet is formed at the proximal end of the cannula. The inlet hole intersects and passes through at least a portion of the plug, thereby forming a distal end of the interior pathway. Moreover, the distal end of the interior pathway is formed such that no blind pocket is formed at the distal end of the cannula. In accordance with further embodiments, the non-circular portion of the cannula can be formed by applying pressure to flatten the cannula body, such that the deformed portion has an oblong or other non-circular cross-section.

Additional features and advantages of embodiments of the present invention will become more readily apparent from the following discussion, particularly when taken together with the accompanying drawings.

BRIEF DESCRIPTION OF THE DRAWINGS

FIG. 1 illustrates a cannula and handle system in elevation in accordance with an embodiment of the disclosed invention;

FIG. 2 is a cross section of the cannula and handle system of the embodiment of FIG. 1 in elevation;

FIG. 3 is a cross section of the cannula and handle system of the embodiment of FIG. 1 in plan view;

FIG. 4 is a cross-section of a cannula in accordance with an embodiment of the disclosed invention in elevation;

FIG. 5 is a cross-section of the cannula of FIG. 3 in plan view;

FIG. 6A is a transverse cross-section of the cannula illustrated in FIG. 4, taken along section line A-A;

FIG. 6B is a transverse cross-section of the cannula illustrated in FIG. 4, taken along section line B-B;

FIG. 8 is a cross-section of a cannula in accordance with other embodiments of the present invention in elevation;

FIG. 9 is a cross-section of the cannula of FIG. 8 in plan view;

FIG. 10 is a cross-section of a cannula in accordance with other embodiments of the present invention in elevation;

FIG. 11 depicts the cannula of FIG. 10 in plan view;

FIG. 12 is a transverse cross-section of the cannula illustrated in FIG. 10, taken along section line F-F;

FIG. 13 is a cross-section of a cannula in accordance with other embodiments of the present invention in elevation;

FIG. 14 is a cross-section of a cannula and handle system in accordance with other embodiments of the present invention.

DETAILED DESCRIPTION

Figure 7A:
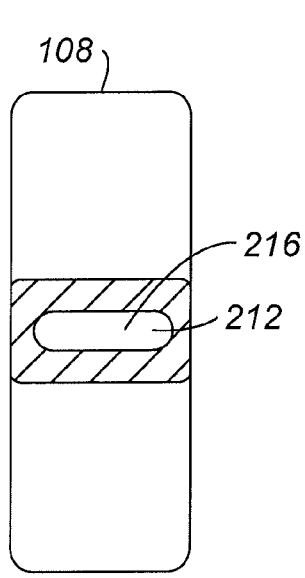
FIG. 7A is a transverse cross-section of a handle as illustrated in FIG. 2, taken along section line C-C.

A cannula and handle system 100 in accordance with embodiments of the disclosed invention is illustrated in elevation in FIG. 1. The cannula and handle system 100 includes a cannula 104 and a handle 108. The cannula 104 includes a distal or anterior portion 112 that includes a tip 114 and an inlet 116 made up of a plurality of holes 120. The cannula 104 further includes a proximal or posterior portion 124 that includes an outlet 128. The cannula 104 generally extends through the handle 108, such that tissue drawn into the inlet 116 is passed to the outlet 128, without contacting any component other than the cannula 104 between the inlet 116 and the outlet 128. The handle 108 may further include a hose or conduit coupler 132 that acts to secure a vacuum hose or conduit to the cannula and handle system 100.

As can be appreciated by one of skill in the art, when the cannula and handle system 100 is in use, a physician or other practitioner inserts the inlet 116 of the cannula 104 into an area of a body from which tissue is to be extracted. Extraction of tissue is generally performed in association with the application of a vacuum at the holes 120 of the inlet 116, by connecting the outlet 128 of the cannula 104 to a vacuum source. For example, a first end of a length of tubing that is connected to the vacuum source at a second end of the tubing can be connected to the conduit coupler 132 such that the outlet 128 is positioned within the tubing. As can also be appreciated by one of skill in the art, tissue collected at the inlet 116 of the cannula 104 and passed through the outlet 128 of the cannula 104 may be deposited into a collection vessel for processing (e.g., washing or treatment) and reinjection into the body at a selected location.

FIG. 2 illustrates the system 100 of FIG. 1 in cross section. As shown in FIG. 2, the cannula 104 includes an interior pathway or tissue transport channel 204 that extends from the tip 114 of the distal portion 112 of the cannula 104 to the outlet 128 of the cannula 104. In addition, it can be seen that tissue drawn in through the inlet 116 and passed to the outlet 128 does not come into contact with any other component of the system 100 other than the interior pathway 204 of the cannula 104. In addition, it can be seen that the interior pathway 204 contains no drop-offs, blind pockets, or other discontinuities that might trap collected tissue and make cleaning difficult or impossible. Instead, the interior pathway 204 is smoothly contoured. Accordingly, the risk of infection can be reduced when extracted tissue is to be reinjected. FIG. 2 also illustrates a shoulder or ramped portion 208 of the cannula 104 corresponding to a change in the contour of the exterior of the cannula 104. The change in the contour of the outer surface of the cannula 104 is generally mirrored by the receiving channel 212 of the handle 108. In particular, the shoulder portion 208 of the cannula 104 corresponds to a transition from an oval cross-section between the distal edge of the shoulder 208 and the tip 114 (see FIG. 6A), and a round cross-section between a proximal edge of the shoulder 208 and the outlet 128 (see FIG. 6B). In order to attach the cannula 104 to the handle 108, the proximal end 124 of the cannula 104 is inserted into the distal end 216 of the handle's receiving channel 212.

Figure 7B:
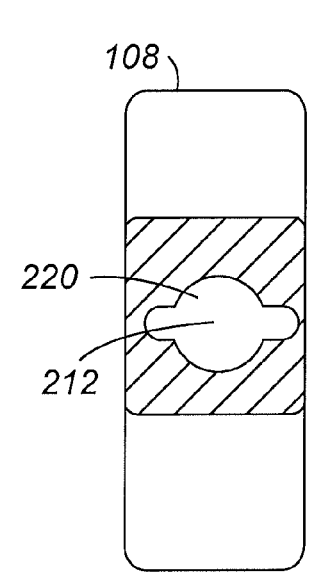
FIG. 7B is a transverse cross-section of a handle as illustrated in FIG. 2, taken along section line D-D.
Figure 7C:
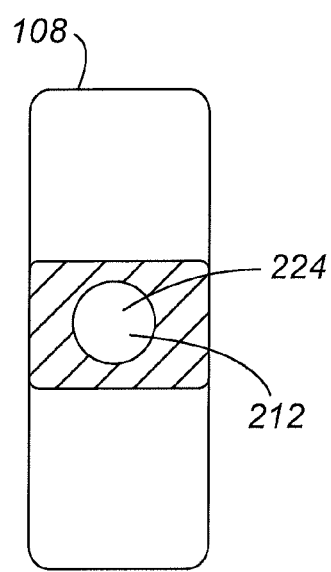
FIG. 7C is a transverse cross-section of a handle as illustrated in FIG. 2, taken along section line E-E.

In general, the distal portion of the receiving channel 212 can feature an oval cross-section (see FIG. 7A) between a tapered or transition portion 220 (see FIG. 7B), corresponding to the shoulder 208 of the cannula 104 when the cannula 104 is fully inserted in the handle 108, and the distal end 216 of the receiving channel 212. The proximal end 224 of the receiving channel 212 has a round cross-section (see FIG. 7C) sized to fit closely to the round cross-section of the proximal end 124 of the cannula 104. In order to pass the proximal end 124 of the cannula 104 through this oval portion of the receiving channel 212, the oval portion of the receiving channel 212 can be sized with a tolerance that allows the round cross-section of the proximal end 124 of the cannula 104 to be accepted. More particularly, the round outer diameter of the proximal portion 124 of the cannula 104 can pass through the distal portion 216 of the receiving channel 212. In accordance with embodiments of the disclosed invention, the proximal portion 124 of the cannula 104 might undergo some deformation while the cannula 104 is being inserted into the handle 108, as the cannula 104 will generally fit tightly within the channel 212 of the handle 108. In addition, the proximal portion 224 of the receiving channel 212 may be sized such that it features an inner diameter that is the same or close to the outer diameter of the proximal portion 124 of the cannula 104. Moreover, the difference in width of the cannula 104 between the outside diameter of the round portion and the major axis 604 (see FIG. 6A) of the ellipse or oval cross-section of the distal portion 112 of the cannula 104 may, in combination with the tapered portion 220 of the receiving channel 212, create a stop. For example, as illustrated in FIG. 3, when the receiving channel 212 is considered in plan view, the tapered portion 220 causes the width of the receiving channel 212 to decrease along the tapered portion 220 from the distal portion 216 to the proximal portion 224. Moreover, this arrangement can provide a friction fit with a positive stop that prevents the cannula 104 from traveling in a more posterior direction relative to the handle 108. As can be appreciated by one of skill in the art, when the system 100 is in use, the forces on the cannula 104 will tend to keep the cannula 104 seated securely in the handle 108. Therefore, the cannula 104 can be secured to the handle 108 without requiring the inclusion of any additional mechanisms, such as a coupler, or potting material. In addition, the cannula can be removed from the handle 108 by pushing the proximal end 124 of the cannula 104 that extends from the proximal end of the handle 108 in a distal direction. In accordance with other embodiments, a coupler or locking mechanism can be integrated into the system 100 as an additional means by which the cannula 104 can be secured to the handle 108.

FIG. 4 is a cross-section of the cannula 104 of FIG. 1-3 in elevation. As discussed above, the distal portion 112 of the cannula 104, including at section line A-A, has an oblong or oval transverse cross-section as illustrated in FIG. 6A. The proximal portion 124 of the cannula 104, including at section line B-B, has a circular transverse cross-section as illustrated in FIG. 6B. A cross-section of this same cannula in plan view is illustrated in FIG. 5.

The cannula 104 illustrated in FIGS. 1-5 features a oblong distal portion 124 and an inlet 116 that includes 24 holes 120. These holes 120 can be distributed around the tip 114 of the cannula 104. For example, the holes 120 can have a 3600 distribution as shown. In accordance with embodiments of the disclosed invention, the holes 120 of the inlet 116 may extend for a distance of from ½ to 2 inches from the tip 114 of the cannula 104. In accordance with still other embodiments, the holes 120, which can vary in number, extend for a distance of 1½ inches from the tip 114. The holes 120 each have an area that is less than the area of the channel 204 through the cannula 104. That is, the area A of the channel 204 (see FIG. 6) is greater than the area of each individual hole 120. In accordance with embodiments of the disclosed invention, the holes 120 are round. The holes 120 may be sized so that they are at least 0.0005" smaller in diameter than the inner diameter of the interior pathway 204 of the cannula 104. For cannulas 104 with an oblong transverse cross-section, the holes may be sized so that they are at least 0.0005" smaller in diameter than the dimension of the inner pathway along the minor axis 608 of the interior pathway 204 (see FIG. 6). In addition, the forward or distal most extent of the channel 204 at the tip 114 of the cannula 104 is defined by the leading edge of the pair of holes 120 closest to the tip 114 of the cannula 104. Accordingly, the creation of blind pockets, which are difficult or impossible to clean, is avoided.

FIGS. 8 and 9 illustrate a cannula 104 in accordance with other embodiments of the disclosed invention. The cannula 104 includes an inlet 116 having four holes 120. The cannula 104 may otherwise be the same or similar to the cannula 104 illustrated in FIGS. 1-5, in that it includes a distal portion 112 that is oblong in cross-section and a proximal portion 124 that is round in cross-section. Accordingly, different cannulas 104 may be used in association with a common handle 108 design. Moreover, it should be appreciated that a cannula 104 in accordance with embodiments of the disclosed invention can have any number of holes. For embodiments in which a high rate of tissue collection is desired, a greater number of holes 120 is generally preferable.

In accordance with further embodiments of the disclosed invention, the cannula 104 has no holes on the top surface to eliminate the possibility of sucking the dermis into the open holes 120 of the cannula 104. A cannula 104 with no holes on a top surface is illustrated in FIG. 10 in elevation, and in FIG. 11 in plan view. In such an embodiment, all holes 120 of the inlet 116 are placed on the sides and the underside of the cannula 104. For example, the top 90° of the cannula 104 is entirely without holes 120, with all holes 120 being within the 270° that include the bottom and sides of the cannula 104 (see FIG. 12). By providing a cannula without holes along substantially one surface, dissection close to the skin is facilitated by eliminating the possibility of sucking the dermis into the open holes 120 of the cannula 104.

The cannula illustrated in FIGS. 10 and 11 also illustrates the inclusion of an air hole 1004. When the cannula 104 is in use, the air hole 1004 admits air into the interior pathway 204. The admission of air through the air hole 1004 can speed the harvest of fat by allowing a bubble of air to enter the interior pathway 204 and accompany the fat in transit. This is believe to speed the harvest by providing a cushion of air. The air is also believed effective in protecting the fat cells from damage. As illustrated, the air hole 1004 can be located anywhere along the length of the cannula 104, between the inlet 116 and the outlet 128. In accordance with embodiments of the disclosed invention, the air hole 1004 is located at some distance from the inlet 116, at a location that would not normally be placed inside a body while fat is being harvested. An air hole 1004 as illustrated in FIGS. 10 and 11 can be included in any cannula 104 in accordance with embodiments of the disclosed invention. As an example, the air hole 1004 may have a diameter of ¹⁄₆₄ of an inch. In accordance with still other embodiments, more than one air hole 1004 may be provided.

The cannulas 104 illustrated in FIGS. 1-12 feature an oblong (in cross section) distal section 112 that can reduce damage to the dermis. In particular, by featuring relatively flat surfaces there is less cannula apex near the dermis, and damage to the dermis adjacent the incision created in order to insert the cannula 104 into the body can be reduced. In other applications, especially those involving deeper dissection away from the dermis, and/or for particular practitioners, a round cross-section cannula may be desirable. Accordingly, as illustrated in FIG. 13, a cannula 104 in accordance with embodiments of the disclosed invention may have a round transverse cross-section. In addition, whether the distal portion 112 features an oblong, circular, or other transverse cross-section, the inlet 116 may incorporate different numbers of holes 120 in different designs or patterns. These different patterns may include providing a hole or holes 120 along one side of the cannula 104 only.

FIG. 14 illustrates a two piece model or system 100' in accordance with other embodiments of the disclosed invention. The system 100' includes a cannula 104 that is provided in two sections, a proximal section 240, and a distal section 244. The proximal section 240 may be fixed to the handle 108, for example by a threaded portion 248. The proximal portion 240 may also incorporate a connector 252 that engages a mating connector 256 provided as part of the distal section 244 of the cannula 104. In common with other embodiments is a channel 204 that extends from adjacent the tip 114 to the outlet 128, and that is without drop-offs, blind pockets, or other discontinuities. Accordingly, the entire extent of the channel 204 is accessible, and therefore cleaning is facilitated. By providing a cannula 104 in two sections, cleaning can be further facilitated, for example by allowing the overall length of the cannula 104 to be reduced in order to place the instrument in an autoclave or other cleaning apparatus that is too small to receive the full length of the assembled cannula 104.

Figure 15:
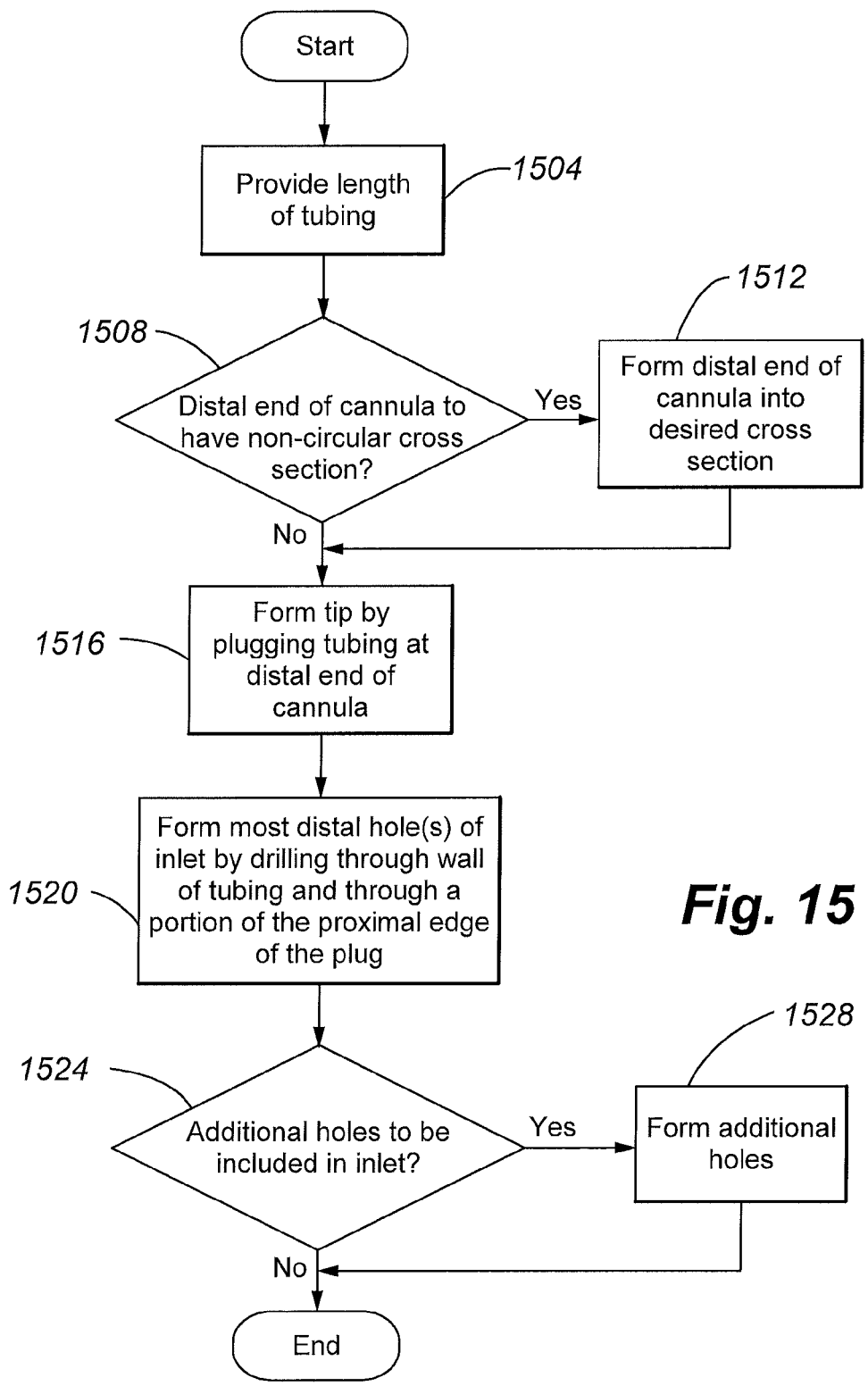
FIG. 15 is a flow chart illustrating aspects of a process for producing a cannula in accordance with embodiments of the present invention.

With reference now to FIG. 15, aspects of a process for producing a cannula in accordance with embodiments of the present invention are illustrated. Initially, a length of tubing is provided (step 1504). For example, the tubing may comprise an 18 inch length of stainless steel tubing having an inside diameter of 0.100 to 0.115 inches and an outside diameter of 0.120 to 0.130 inches. A determination may then be made as to whether the distal end 112 of the cannula is to have a non-circular cross-section (step 1508). If the distal end of the cannula is to have a non-circular cross-section, the distal end 112 of the cannula 104 is formed into the desired cross-section (step 1512). For example, where the distal end 112 of the cannula 104 is to have an oblong or oval cross-section, a flat plate of a predetermined thickness is placed inside of the tubing, and the distal end 112 is placed between two parallel plates that are brought together to produce the desired profile in the distal portion 112 and at the transition or ramped portion 208.

After shaping the distal end 112 of the cannula 104 at step 1512, or after determining at step 1508 that the distal end 112 of the cannula 104 is to have a circular cross-section, the tip 112 is formed by plugging the tubing at the distal end 112 (step 1516). For example, plugging the tubing at the tip 112 may comprise welding a plug of metal into the interior diameter of the tubing at the tip. The most distal hole or holes 120 of the inlet 116 are then formed by drilling through the wall of tubing and through a portion of the proximal edge of the plug (step 1520). The holes 120 can also be formed using electrochemical means or electrical discharge techniques. By intersecting the proximal edge of the plug when drilling an inlet hole 120, the creation of a blind pocket between the forward end of the cannula channel 204 and the inlet hole 120 is prevented. Instead, the most distal end of the channel 204 coincides with the most distal edge of the hole 120. Moreover, in accordance with embodiments in which a pair of holes 120 are opposite one another, the ability to clean the forward extent of the channel 204 can be further facilitated. After forming the most distal holes 120, a determination may be made as to whether additional holes 120 are to be included in the inlet 116 (step 1524). If additional holes are to be included in the inlet 116, those additional holes may be formed (step 1528). The process for forming a cannula 104 may then end.

As can be appreciated by one of skill in the art, other or alternative steps may be included in a process for forming a cannula 104. Moreover, where the cannula is to include provisions for a mechanical coupler, for instance to provide additional means for securing the cannula 104 to the handle 108, or in connection with embodiments incorporating a two-piece cannula 104, additional features may be formed on the cannula components. In addition, additional features, such as flanges along a proximal portion of the cannula, to facilitate securing the cannula 104 within the receiving channel 212 of the handle 108, or other such features can be formed. Moreover, additional features can be incorporated into the inlet 116. For instance, the outer surface of the cannula 104 adjacent the holes 120 can be raised or lifted, forming a rasp, to facilitate breaking up tissue during tissue collection. Formation of the cannula 104 can also include coating the interior pathway 204 with a silicone material. By coating the interior pathway 204 with silicone, rough areas are smoothed, and there is less chemical and physical trauma to fat cells. A silicone coating can also facilitate approval of system components for medical use. In addition, the cannula 104 can be polished mechanically or electrochemically, and passivation treatment can be performed with nitric acid or other substances to rid the cannula 104 of metal dust and micro abrasions. A system 100 in accordance with embodiments of the disclosed invention may be provided as a durable and/or a disposable device. Moreover, components of the system 100 may be durable, while other components may be disposable. By providing a system 100 in which some or all of the components are disposable, a system 100 may be constructed less expensively than a comparable system 100 that is intended to be durable.

Systems 100 in accordance with embodiments of the disclosed invention can also include features to increase the speed of fat or tissue harvest. Such features can include cannulas 104 that are relatively short in length (e.g., less than 17 inches), cannulas of relatively large diameter (e.g., up to 10 mm), the inclusion of a cannula air hole or air holes 1004, holes 120 that are relatively small in diameter (e.g., less than 0.054 inches), inlet holes 120 that span up to 2 inches of the length of the cannula 104, inlet holes 120 that are as numerous as possible, and holes 120 that are round, rather than oblong or other shapes. In addition, features can be incorporated that promote the survival of fat cells and adult stem cells can be incorporated. Such features can include inlet holes 120 that are relatively small (e.g., less than 0.054 inches), the provision of a substantially continuous interior pathway 204 that avoids or eliminates drop offs and pockets and in which the pathway 204 of the cannula 104 extends through the handle 108, a handle 108 with a receiving channel 212 that is substantially continuous and that eliminates drop offs and pockets, inlet holes 120 with dull edges to reduce damage to cells, cannulas 104 that are relatively short (e.g., less than 5 cm), inlet holes 120 that are round to produce parcels of fat that are less likely to be damaged during transit through the system 100, the inclusion of one or more air inlet holes 1004 to provide a cushion of air for fat parcels during passage through the system 100, the option of a disposable system 100 or components of the system 100 to lessen the likelihood of infection, the inclusion of a silicon inner coating to smooth rough spots and decrease the chance of chemical or physical trauma to fat cell parcels, the provision of a closed system to reduce the introduction of ambient air and bacteria, viruses, dust or other contaminants with the air, and/or the elimination of blind pockets at the tip 114 of the cannula 104. Still other of the disclosed features can be included to decrease the formation of ripples in the skin, such as flattening the dissecting end of the cannula 104 to an oval or a rectangle to reduce the cannula apex near the dermis. In still other aspects, a system 100 in accordance with embodiments of the disclosed invention can be produced economically, in that there is no cost for potting the cannula 104 in the handle 108, the provision of embodiments that eliminate or reduce the need for Luer locks, screw or o-ring type connectors, or other connectors, and/or the provision of a handle 108 that can be used with different cannula 104 configurations.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. A cannula system, comprising:
   a rigid cannula, including:
      a first end;
      a second end;
      an interior pathway extending from proximate the first end to the second end;
      an inlet at the first end, wherein the inlet includes at least a first hole and a second hole, and wherein a leading edge of the first and second holes defines a forward-most extent of the interior pathway of the cannula;
      an outlet at the second end;
   a handle, including:
      a first end;
      a second end;
      a receiving channel, wherein the receiving channel includes a first opening at the first end of the handle and a second opening at the second end of the channel, wherein the rigid cannula is received by the receiving channel and extends between the first and second ends of the handle, wherein the rigid cannula has an outer diameter, wherein at least a first section of the outer diameter of the rigid cannula has a non-circular cross section, and wherein at least a first section of the receiving channel of the handle has a non-circular cross section to receive the first section of the outer diameter of the cannula.

2. The system of claim 1, wherein the interior pathway is substantially continuous.

3. The system of claim 1, wherein the area of the interior pathway is substantially constant from the inlet to the outlet.

4. The system of claim 1, wherein the inlet includes a plurality of holes, including the first and second holes, wherein at least the first and second holes are adjacent the forward-most extent of the interior pathway, and wherein the forward-most extent of the interior pathway lies along a line between a forward-most extent of the first hole and a forward-most extent of the second hole.

5. The system of claim 4, wherein the plurality of holes are included within a length of the cannula extending less than two inches from the first end of the cannula.

6. The system of claim 4, wherein an area of each hole in the plurality of holes is less than an area of the interior diameter of the interior pathway of the cannula.

7. The system of claim 1, wherein the non-circular cross section of the first section of the outer diameter of the rigid cannula is oblong, wherein the non-circular cross section of the first section of the receiving channel of the handle has an outer diameter that is oblong, wherein the oblong cross section of the first section of the outer diameter of the rigid cannula includes the first end of the rigid cannula, and wherein a second section of the outer diameter of the rigid cannula has a round cross section.

8. The system of claim 7, wherein the first opening of the receiving channel is oblong and wherein the second opening of the receiving handle is round.

9. The system of claim 1, wherein while the cannula is received by the receiving channel of the handle, the second end of the cannula extends from the second end of the handle and the first end of the cannula extends from the first end of the handle.

10. The system of claim 9, wherein the cannula includes first and second sections, wherein the first section is fixed to the handle, and wherein the second section is interconnected to the first section by a coupler.

11. The system of claim 9, wherein the handle includes a surface that is operable to engage a vacuum tube, whereby a vacuum can be formed about the outlet of the cannula.

12. The system of claim 1, wherein the interior pathway of the cannula includes a silicone coating.

13. The system of claim 1, further comprising:
   an air hole, located between the inlet and the outlet of the cannula, wherein the interior pathway is in communication with a surrounding atmosphere through the air hole.

14. The cannula system of claim 1, wherein the cannula further includes:
   a tip, wherein the tip is the only portion of the cannula that extends forward of the forward-most extent of the interior pathway.

15. The cannula system of claim 1, wherein the rigid cannula is received by the handle such that the first end of the rigid cannula extends from the first end of the handle and such that the second end extends from the second end of the handle, and wherein the rigid cannula cannot be received by the handle such that the first end of the rigid cannula extends from the second end of the handle and such that the second end extends from the first end of the handle.

* * * * *